US00PP09258P

United States Patent [19]

Hoff

[11] Patent Number: Plant 9,258

[45] Date of Patent: Aug. 22, 1995

[54] VARIETY OF LILIUM NAMED 'HOLECA'

[75] Inventor: Petrus M. M. Hoff, Steenbergen, Netherlands

[73] Assignee: Hoffgaarde B.V., Steenbergen, Netherlands

[21] Appl. No.: 312,211

[22] Filed: Sep. 26, 1994

[51] Int. Cl.[6] ..... A01H 5/00

[52] U.S. Cl. ..... Plt./87.4

[58] Field of Search ..... Plt. 87.4

[56] References Cited

U.S. PATENT DOCUMENTS

P.P. 4,176 1/1978 McRae ..... Plt./87.4

P.P. 7,100 1/1990 Vletter ..... Plt./87.4

*Primary Examiner*—James R. Feyrer

*Attorney, Agent, or Firm*—Webb Ziesenheim Bruening Logsdon Orkin & Hanson

[57] ABSTRACT

A new and distinct cultivar of lily plant named Holeca, particularly characterized by orange-red lasting color of the flowers, height of 90–100 cm, pedicel of 10–12 cm in length with 3–5 flowers, broad, dark green leaves, produced 40–60 stem bulblets, very fast growing to flowering and capable of producing stems and flowers for cut-flower production.

1 Drawing Sheet

BACKGROUND OF THE INVENTION

The present invention comprises a new and distinct cultivar of lily, botanically known as Lilium and asiatic and hereinafter referred to by the cultivar name Holeca.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde B. V., Franseweg 9, 4651 PV Steenbergen, The Netherlands in 1989. The female and male parents were seedlings originated by Applicant, which were proprietary and maintained by Applicant for breeding purposes.

The new cultivar was discovered and selected as one flowering plant within the progeny of the stated cross by the inventor on May 15, 1991 in a controlled environment in Steenbergen.

The first act of asexual reproduction of the new cultivar was accomplished by the inventor when scales were taken from the initial selection in Oct. 31, 1991 in a controlled environment in Steenbergen.

Horticultural examination of clonal specimens initiated Apr. 2, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice.

The following traits have been repeatedly observed and are determined to be basic characteristics of the new cultivar which in combination distinguish the lily as a new and distinct cultivar.

1) Orange-Red flowers and buds which hold color over time.

2) Plant height of 90–100 cm.

3) Pedicel 10–12 cm in length with 3–5 flowers.

4) Broad dark green leaves.

5) Produces 40–60 stem bulblets.

6) Very fast growing to flowering, approximately 70 days at 15° C.

DESCRIPTION OF THE DRAWING

The accompanying color photographic drawing shows typically flower characteristics of the new cultivar, with colors being as true as possible with illustrations of this type.

DESCRIPTION OF THE NEW PLANT

In the following description, color references are made to The Royal Horticultural Society Colour Chart. The color values were determined at Steenbergen on Apr. 2, 1992.

THE PLANT

Classification:

*Botanic.*—Lilium asiatic.

*Commercial.*—Hybrid asiatic lily for cut-flower production.

Form: Single upright stem from each bulb.

*Height.*—90–100 cm.

*Growth habit.*—Upright.

Stem:

*Diameter.*—1 cm average.

*Shape.*—Rounded.

*Color.*—Yellow-Green Group 147A.

*Bulblets.*—Stem bulblets, 40–60 on average; Greyed-Purple Group 187A.

Foliage:

*Quantity.*—75–90 (provide quantity range).

*Size of leaf.*—12 cm maximum length; breadth up to 3 cm.

*Shape of leaf.*—Broad elliptic.

*Texture of leaf.*—Smooth.

*Color.*—Yellow-Green Group 147A.

Bulbs:

*Size.*—12–14 cm in circumference.

*Color.*—White.

THE BUD

Form: Narrow, oblong, rounded ends.
Size: 10 cm in length.
Color: Orange-Red Group 34A.
Shape: Oblong (UPOV Type II).

THE FLOWER

Blooming habit: 70 days after planting.
Size: 15 cm in diameter.
Borne: Umbrellate, single.
Tepalage:
*Number of tepals.*—6.
*Arrangement.*—Hexagonal.
*Color.*—Upper surface: Orange-Red Group 34A; holds color over time and not affected by prolonged sun exposure. Lower surface: Orange-Red Group 34A.
*Spotting.*—Very lightly spotted on inner and outer tepals; spots are about 1 mm in diameter and are in throat halfway area; spots are not easily seen and are Greyed-Purple Group 187A. Surface: Smooth, shiny and thick feeling, like velvet. Texture: Smooth, no papillae.
Pedicel:

*Length.*—10 cm.
*Form.*—Upright.
Nectaries;
*Shape.*—Very small and hard to see because color is same in tepals, viz Orange-Red Group 34A.
*Length.*—About 1.4 cm.
Disease resistance: No unusual problems have been observed.
Fragrance: None.
Lasting quality: 10 days in water at room conditions after cutting.

REPRODUCTIVE ORGANS

Stamens:
*Number.*—6.
*Length.*—6 cm.
Pistils:
*Number.*—1.
*Stigma and style color.*—Orange-Red Group 34A.
*Ovaries—color.*—Yellow-Green Group 145A.

I claim:

1. A new and distinct variety of lily plant substantially as shown and described.

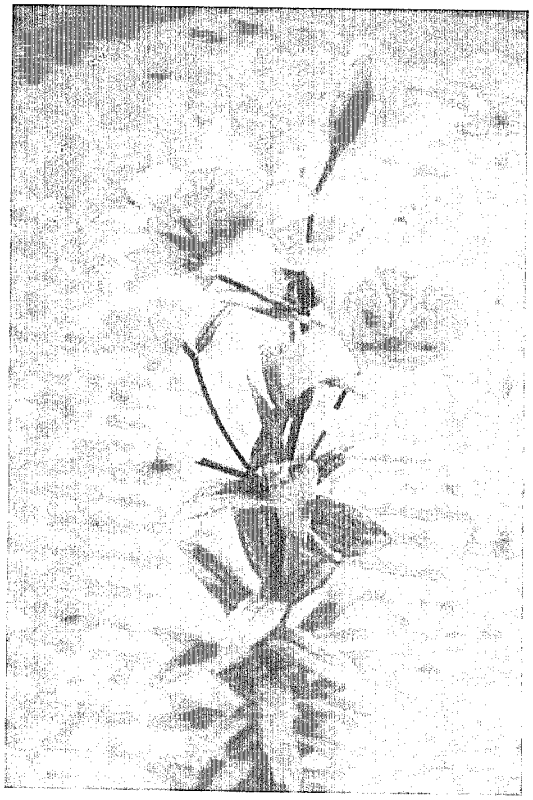

* * * * *